United States Patent
Sandrin et al.

(10) Patent No.: US 9,918,695 B2
(45) Date of Patent: Mar. 20, 2018

(54) METHOD FOR MEASURING AT LEAST ONE PROPERTY OF BIOLOGICAL TISSUE

(75) Inventors: Laurent Sandrin, L'Hay les Roses (FR); Véronique Miette, Villejuif (FR); Magali Sasso, Paris (FR)

(73) Assignee: Echosens, Paris (FR)

(*) Notice: Subject to any disclaimer, the term of this patent is extended or adjusted under 35 U.S.C. 154(b) by 0 days.

(21) Appl. No.: 13/496,628

(22) PCT Filed: Sep. 17, 2010

(86) PCT No.: PCT/EP2010/063677
§ 371 (c)(1),
(2), (4) Date: Apr. 10, 2012

(87) PCT Pub. No.: WO2011/033050
PCT Pub. Date: Mar. 24, 2011

(65) Prior Publication Data
US 2012/0190983 A1    Jul. 26, 2012

(30) Foreign Application Priority Data
Sep. 17, 2009  (FR) ..................... 09 56408

(51) Int. Cl.
*A61B 8/08* (2006.01)
*A61B 5/00* (2006.01)
*A61B 8/00* (2006.01)

(52) U.S. Cl.
CPC .............. *A61B 8/08* (2013.01); *A61B 5/0051* (2013.01); *A61B 5/415* (2013.01); *A61B 5/418* (2013.01); *A61B 8/42* (2013.01); *A61B 8/485* (2013.01)

(58) Field of Classification Search
CPC ....... A61B 5/0048; A61B 5/415; A61B 5/418; A61B 8/08; A61B 8/42; A61B 8/485
(Continued)

(56) References Cited

U.S. PATENT DOCUMENTS 4,389,893 A * 6/1983 Ophir ....................... A61B 8/08
73/599
4,441,368 A   4/1984 Flax
(Continued)

FOREIGN PATENT DOCUMENTS

EP    1 629 777 A1    3/2006
WO    WO 2007/100107    9/2007
(Continued)

OTHER PUBLICATIONS

International Search Report as issued for PCT/EP2010/063677.

*Primary Examiner* — Katherine Fernandez
(74) *Attorney, Agent, or Firm* — Pilsbury Winthrop Shaw Pittman LLP

(57) ABSTRACT

A method for measuring at least one property of biological tissue, including: positioning an ultrasonic transducer opposite the biological tissue to be measured; generating an ultrasonic signal within the biological tissue; acquiring at least one ultrasonic signal reflected by the biological tissue; determining at least one parameter of the biological tissue using the acquisition of the ultrasonic signal reflected by the biological tissue, the at least one parameter being representative of the biological tissue; comparing the at least one parameter of the biological tissue with at least one reference parameter of a target biological tissue so as to confirm the hypothesis of the presence of the target biological tissue opposite the ultrasonic transducer; and determining at least one property of the biological tissue on the basis of the result of the comparison. The method can be directly used in the field of humans or animals.

13 Claims, 1 Drawing Sheet

(58) Field of Classification Search
USPC .......................... 600/438, 437, 442; 382/128
See application file for complete search history.

(56) References Cited

U.S. PATENT DOCUMENTS

| | | | | |
|---|---|---|---|---|
| 4,603,703 | A * | 8/1986 | McGill et al. | 600/544 |
| 5,906,578 | A * | 5/1999 | Rajan et al. | 600/424 |
| 6,013,031 | A * | 1/2000 | Mendlein et al. | 600/442 |
| 6,238,342 | B1 * | 5/2001 | Feleppa et al. | 600/437 |
| 8,131,379 | B2 * | 3/2012 | Hauck | 607/101 |
| 2002/0068870 | A1 | 6/2002 | Alam et al. | |
| 2005/0203398 | A1 * | 9/2005 | Sandrin et al. | 600/438 |
| 2008/0129732 | A1 * | 6/2008 | Johnson et al. | 345/424 |
| 2008/0281196 | A1 * | 11/2008 | Sornes | A61B 5/02007 600/437 |
| 2010/0168574 | A1 * | 7/2010 | Takabayashi | A61B 8/08 600/443 |

FOREIGN PATENT DOCUMENTS

| WO | WO 2008/139245 | 11/2008 |
|---|---|---|
| WO | WO 2009/107673 | 9/2009 |

* cited by examiner

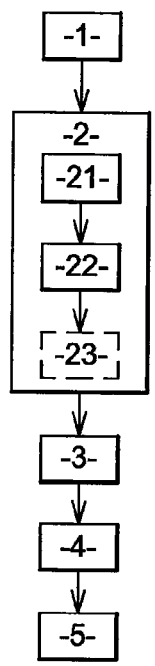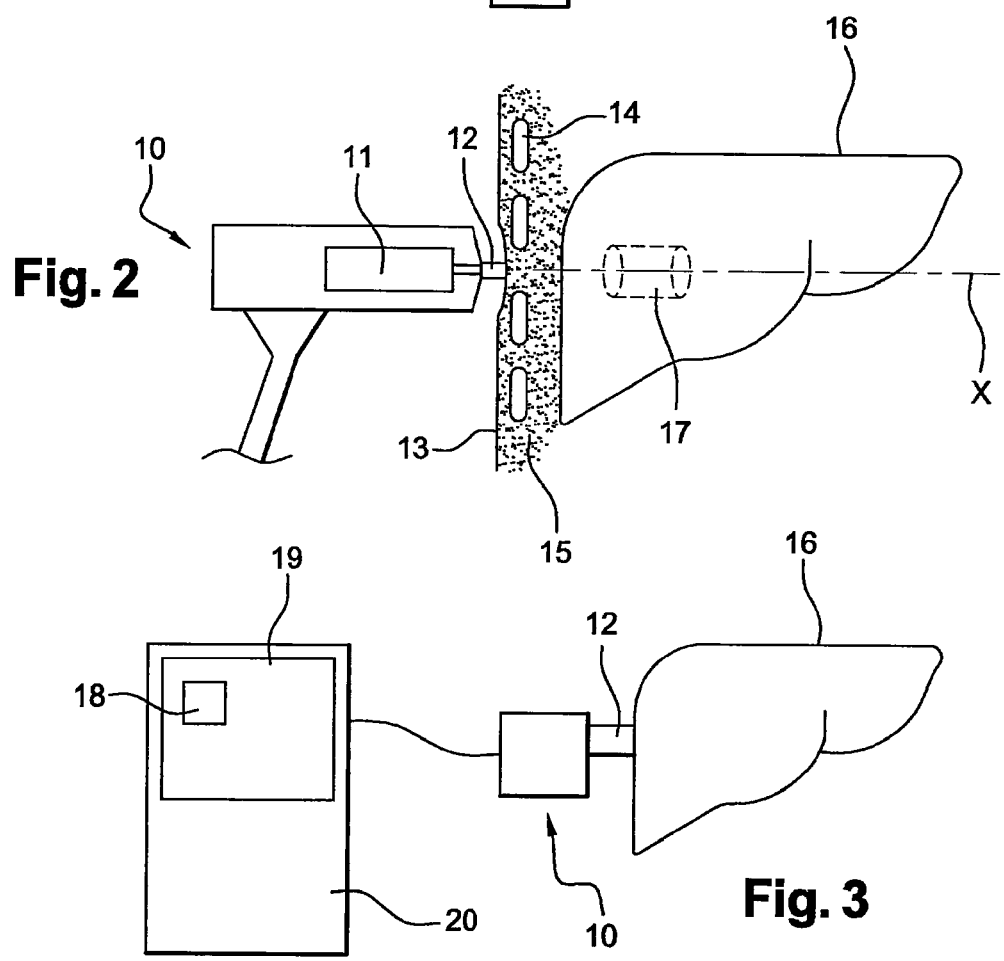

METHOD FOR MEASURING AT LEAST ONE PROPERTY OF BIOLOGICAL TISSUE

CROSS REFERENCE TO RELATED APPLICATIONS

This application is the U.S. National Stage of PCT/EP2010/063677, filed Sep. 17, 2010, which in turn claims priority to French Patent Application No. 0956408, filed Sep. 17, 2009, the entire contents of all applications are incorporated herein by reference in their entireties.

The invention relates to a method for measuring at least one property of biological tissue. It is applicable particularly in the field of human or animal tissue.

In order to ascertain the viscoelastic properties of biological tissue, one method known and commonly used is to measure these properties with pulsed elastography, as is described for example in patent application number FR 2843290. The method disclosed in this document consists in placing a probe comprising an ultrasonic transducer and a low frequency vibration generator in contact with the epidermis, and more particularly opposite the biological tissue to be measured. A low frequency elastic wave is then generated in the biological tissue by means of a low frequency vibration generator. At the same time, ultrasonic signals are emitted and acquired via an ultrasonic transducer while the low frequency elastic wave is being propagated so that the displacement of the biological tissue exposed to the low frequency elastic wave may be observed. Values are then calculated on the basis of this displacement.

One drawback of this prior art consists in that the operator is not able to affirm with certainty that the ultrasonic transducer is positioned opposite the tissue that is to be measured. Consequently, it is possible that the values obtained by implementing such a method may not be representative of the tissue the operator is trying to measure.

Since the values depend particularly on the position of the probe, which is positioned approximately by the operator based on his technical knowledge, the skill and technical experience of the operator have a very strong influence on the values obtained. These values thus depend in large degree on the operator and the implementation of such a procedure requires that the operator has acquired considerable experience working in the human or animal realm.

The purpose of the invention is therefore more specifically to address the disadvantages of the method described in the preceding. In this context, the object of the invention is to suggest a method for measuring properties of biological tissue corresponding to the tissue the operator wishes to measure. A further object of the invention is to suggest a method for measuring properties of biological tissue that does not rely on the operator having acquired extensive experience in the human or animal realm.

To this end, the invention relates to a method for measuring at least one property of a biological tissue, comprising the steps of:
  positioning an ultrasonic transducer opposite the biological tissue to be measured;
  generating at least one ultrasonic signal within said biological tissue;
  acquiring at least one ultrasonic signal reflected by said biological tissue;
  determining at least one parameter of said biological tissue by means of said acquisition of the at least one ultrasonic signal reflected by the biological tissue, said at least one parameter being representative of said biological tissue;

this method being characterized in that it further comprises the steps of:
  comparing said at least one parameter of said biological tissue with at least one reference parameter of a target biological tissue so as to confirm the hyphothesis of the presence of said target biological tissue opposite said ultrasonic transducer;
  determining at least one property of said biological tissue on the basis of the result of said comparison step.

For the rest of this description, the term parameter is understood to mean a measurable value or a combination of measurable values that is or are able to correspond to a characteristic that may be physical, physiological, viscoelastic or ultrasonic in nature, or any other characteristic of a medium such as a biological tissue. For the purposes of the invention, the parameter is intended to affirm the hypothesis of the present of target tissue opposite the ultrasonic transducer when compared with a reference parameter of the biological tissue, which may be, but is not limited to, a reference value, a range of reference values, a reference matrix or a reference template, which have been determined empirically. The comparison may also consist in determining a physiological phenomenon such as the detection or failure to detect a shear wave that is propagated through the biological tissue.

For the rest of this description, the term property is understood to mean a value representative of an intrinsic characteristic of a medium such as biological tissues. This property may result from a measurement or it may be determined by a physical or physiological type model described by a series of parameters.

According to the preceding definition, the parameter may be made up of the central ultrasonic signal frequency reflected back by the biological tissues. The associated property may be for example ultrasonic attenuation, which is linked by a physical model to the weakening of the central frequency in biological tissues.

In general, a measured value may be both a parameter and a property. For example, weight is both a value measured by a scale (parameter) and a property of a body.

With the aid of the invention, the presence of a target biological tissue is confirmed before at least one property of the biological tissue is determined, or it is confirmed at the same time as at least one property of the biological tissue is determined provided that at least one determined parameter matches at least one corresponding reference parameter. Consequently, the properties determined by the method according to the invention effectively correspond to the properties of the desired biological tissue. It is this feature that makes this method particularly easy to use by the operator, and it is no longer essential for the operator to possess extensive knowledge of the human or animal fields in order to be able to implement the method in accordance with the invention.

Besides the main characteristics, which have been outlined in the foregoing paragraph, the method for measuring at least one property of biological tissue according to the invention may include one or more additional characteristics from those listed in the following, either individually or in any technical possible combination thereof:
  said comparison step consists in comparing a value of the at least one parameter with a value of the at least one reference parameter, the step of determining the at least one property only being carried out if the absolute value of the difference between the at least one value of this parameter and the value of the at least one reference parameter is less than a given threshold value;

a plurality of parameters are combined together, the comparison step consisting in comparing a result obtained from the combination of parameters with the at least one reference parameter;

the method comprises a step of generating a low frequency elastic wave in the biological tissue;

this low frequency elastic wave is generated by vibration of a low frequency elastic wave generator;

this low frequency elastic wave is generated by radiation pressure;

an indicator informs an operator of this result of this comparison step; such an indicator may be a visual indicator that is located on the probe or on a screen and is capable of communicating with the probe, or it may also be an audible indicator.

said parameter and said property of the biological tissue are determined on the basis of data extracted from the acquisition of the at least one ultrasonic signal reflected by the biological tissue; because of this feature, a single measurement is taken to determine both a representative parameter of said biological tissue and a property of said biological tissue;

the at least one property of said biological tissue is determined by implementing an elastography method;

the at least one property is the elasticity of said biological tissue;

the at least one property is an ultrasonic attenuation of said biological tissue;

the at least one parameter is an ultrasonic parameter of said biological tissue;

the at least one ultrasonic parameter is an ultrasonic attenuation of said biological tissue;

the at least one parameter is a viscoelastic parameter of said biological tissue;

the at least one viscoelastic parameter is the elasticity of said biological tissue;

the elasticity is obtained by a vibration elastography method;

the at least one parameter is a physiological parameter of said biological tissue.

The invention further relates to an ultrasonic transducer with which the method for measuring at least one property of a biological tissue is implemented in accordance with the invention.

Other characteristics and advantages of the invention will be evident from the description thereof that is provided in the following, purely for non-limiting, exemplary purposes, with reference to the accompanying drawing, in which:

FIG. 1 shows a flowchart of the operating principle of a method according to the invention;

FIG. 2 shows a possible implementation example of the method according to the invention;

FIG. 3 shows an example of an ultrasonic transducer according to the invention.

For the sake of clarity, only the elements that are essential for an understanding of the invention have been illustrated, and these are not shown to scale or according to any diagrammatic principle.

It should be noted that a low frequency elastic wave may be for example in the range between 10 and 1000 Hz.

It should be noted that an ultrasonic wave may be in the range from 20 KHz to 1000 MHz.

In a non-limiting example, the biological tissue used in the rest of this description to illustrate the implementation of the method according to the invention is the liver.

The steps necessary for carrying out the method for measuring the at least one property of biological tissue will now be described with reference to FIGS. 1 to 3.

According to a first step 1, an ultrasonic transducer is positioned opposite a biological tissue.

It will be noted that in non-limiting embodiments various types of single element or multi-element ultrasonic transducers may be used. The transducer may be of the wedge, annulus, 2D matrix, linear or convex array type, or it may be of the star array type or any other type of transducer capable of emitting and receiving ultrasonic signals.

In the example of the liver, an ultrasonic probe comprising at least the ultrasonic transducer capable of emitting and receiving ultrasonic signals, is positioned in contact with the epidermis and opposite the liver in such manner that the ultrasonic signals emitted by the probe are able to spread through the liver.

According to a second step 2, at least one parameter of the biological tissue is measured, and this measurement includes a first substep 21 and a second substep 22.

In first substep 21, at least one ultrasonic signal is generated inside the biological tissue by the ultrasonic transducer.

In second substep 22, at least one ultrasonic signal reflected back by the biological tissue is acquired.

In the example of the liver, measurement of at least one parameter is carried out in a region of interest (ROI). The region of interest is located for example between 25 and 65 mm below the epidermis. A parameter of the tissue in the region of interest may be measured for example by means of a vibration elastography procedure using a vibration elastography probe such as is illustrated in FIG. 2.

Thus, in an arrangement of this kind, a third, supplementary substep 23 is necessary. This third substep consists in generating a low frequency elastic wave inside the liver. The propagation of this low frequency elastic wave is followed for example by the generation of the ultrasonic signal (first substep 21) and acquisition of the ultrasonic signal reflected b by the liver (second substep 22).

The sequence of substeps 21, 22 and 23 is provided here for exemplary purposes. They may be effected in a different order.

FIG. 2 shows:

a vibration elastography probe 10 equipped with a low frequency elastic wave generator 11 and an ultrasonic transducer 12;

the epidermis 13;

four ribs 14;

a subcutaneous tissue 15;

a biological tissue formed, for exemplary, non-limiting purposes, by a liver 16;

a region or interest 17;

an axis X of ultrasonic emissions.

In this embodiment, the probe that is positioned in first step 1 is vibration elastography probe 10. In order to determine a viscoelastic parameter of liver 16, during step 1 ultrasonic transducer 12 of probe 10 is positioned in contact with epidermis 13 and in the intercostal space, in other words between two of the four ribs 14. Low frequency elastic wave generator 11 generates one or more low frequency elastic waves through indirect contact with liver 16, and these waves pass through subcutaneous tissue 15 and into liver 16. This (these) low frequency elastic wave(s) is (are) generally obtained by mechanical means, but may equally well be obtained by radiation pressure, by ultrasound hyperthermia, or even by internal vibrations of the body (heartbeat, pulse, or the like). The temporal shape of this (these) low frequency elastic wave(s) may be arbitrary, is more usually pulsed, transient or periodic type (sustained, monochromatic).

At the same time, ultrasonic waves are generated and acquired along axis X by means of ultrasonic transducer 12 for monitoring the propagation of this (these) low frequency elastic wave(s) within region of interest 17, that is to say between 25 and 65 mm below epidermis 13.

According to a third step 3, at least one parameter of the biological tissue is determined by acquisition of at least one ultrasonic signal reflected by the biological tissue, which acquisition takes place during second substep 22. The parameter(s) is (are) representative of the biological tissue.

According to advantageous variants of the method according to the invention, a desired parameter may be a viscoelastic parameter, an ultrasonic parameter or a physiological parameter.

Regarding the viscoelastic parameter, the term viscoelastic parameter of a biological tissue refers in non-limiting manner to at least one mechanical property that describes the viscoelastic behaviour of the biological tissue. The mechanical property may for example be formed by a Young's modulus, a shear modulus, since wave properties propagate in the viscoelastic biological tissue such as an ultrasonic speed, a dispersion at ultrasonic speed, an attenuation of a low frequency elastic wave, or also parameters associated with a viscoelastic model of the biological tissue, such as the Maxwell model, the Voigt model, or the Zener model.

In the example of the liver 16 described previously, viscoelastic parameters are determined.

A first viscoelastic parameter corresponds for example to detection of a low, frequency elastic wave in region of interest 17.

A second viscoelastic parameter corresponds for example to the speed at which this low frequency elastic wave moves inside region of interest 17.

A third viscoelastic parameter corresponds for example to an elasticity value of the biological tissue in region of interest 17.

Thus, three viscoelastic parameters may be deduced from the measurement carried out in second step 2.

Moreover, a parameter of the biological tissue located inside region of interest 17 may be measured using a method other than vibration elastography. For example, parameters may be determined from data that is extracted from the ultrasonic signal reflected by the biological tissue of region of interest 17. Accordingly, a simple ultrasonic emission and acquisition using an ultrasonic transducer 12 are sufficient to enable measurement of a parameter relating to the biological tissue (16) constituted by region of interest 17.

Regarding the ultrasonic parameter, an ultrasonic parameter of a biological tissue is understood in non-limiting manner to be an ultrasonic speed, a measurement of dispersion at ultrasonic speed, an ultrasonic attenuation, or also a coefficient of ultrasonic backscatter.

Additionally, in the temporal domain the ultrasonic parameter may be formed for example by a strength of the ultrasonic signal, an energy of the ultrasonic signal, a correlation or intercorrelation coefficient.

In the spectral domain the ultrasonic parameter may be formed for example by a shift of the central frequency of the received ultrasonic signal relative to the central frequency of the transmitted ultrasonic signal.

The ultrasonic signal may also be obtained in the transformed domains such as for example the time-frequency domain or the cepstral domain.

It is understood that the ultrasonic parameters described in the foregoing are given here for purely illustrative purposes and do not by any means represent an exhaustive list.

Regarding the physiological parameter, the physiological parameter of a biological tissue refers in non-limiting manner to the detection of a flow of blood through the biological tissue or the organic frequency of the biological tissue.

As was indicated earlier, the physiological parameter may be formed by the detection of a flow of blood through the biological tissue.

By way of example, Doppler echography may be carried out to determine whether the region of interest of the biological tissue contains a flow of blood and thus a vein.

According to a fourth step 4, at least one parameter of the biological tissue is compared with at least one reference parameter of a target biological tissue.

In other words, software means, which are not shown, automatically verify that the parameter or parameters determined in third step 3 has/have characteristics essentially similar to the reference characteristics that the target biological tissue comprises. To do this, the viscoelastic and/or ultrasonic and/or physiological reference parameter(s) of the target tissue (the liver 16 in our example) is/are compared with the viscoelastic and/or ultrasonic and/or physiological parameter(s) of the tissue being measured.

By way of example, when the parameter of the biological tissue being measured differs from the reference parameter (which may be constituted by a range of values) of the target biological tissue, an indicator informs an operator of the result of this comparison. Thus, the operator may for example be prompted by a visual indicator 18 that is displayed on a screen 19 included in device 20 (represented in FIG. 3), which device 20 is linked to probe 10 comprising ultrasonic transducer 12, to move probe 10 so that ultrasonic transducer 12 is located opposite the biological tissue the operator wishes to measure. The appearance of visual indicator 18 is a function of the parameter being determined. Without limitation thereof, the appearance of indicator 18 may be formed by a signal lamp that lights up:
  green when the parameter being determined matches the reference parameter;
  red when the parameter being determined differs from the reference parameter.

According to such an embodiment, when visual indicator 18 lights up red, this indicates to the operator that ultrasonic transducer 12 is not situated opposite the biological tissue for which the operator wishes to determine a property.

Steps 1 to 4 are thus repeated until the parameter of the biological tissue located opposite ultrasonic transducer 12 essentially matches the reference parameter of the target biological tissue. This condition may be indicated to the operator example by visual indicator 18 lighting up green. Moreover, the visual indicator may be displayed by an LED (not shown) included in probe 10 that also comprises ultrasonic transducer 12. This LED changes colour depending on the result of comparing the determined parameter with the reference parameter.

The indicator may also have the form of an acoustic indicator.

The indicator may have the form of any other means that informs the operator of the result of comparing one or more determined parameter(s) with one or more reference parameter(s).

According to a different embodiment, when a determined parameter differs from the corresponding reference parameter of the target biological tissue, the operator is not able to determine a property. This inability is not necessarily displayed by means of an indicator. For example, the absence of a value representative of a property obtained subsequently (during step 5) in the display may inform the operator that the ultrasonic transducer is not located opposite the tissue to be measured.

In the example of the liver 16 shown earlier, the presence of propagation of a low frequency elastic wave generated in the course of second step 2 may serve as the viscoelastic parameter of the biological tissue.

As such, it should be noted that ultrasonic transducer 12 of probe 10 is positioned between two of the four ribs 14. Consequently, this positioning prevents access to certain organs, the thyroid for example. However, this positioning may allow access to the lungs, the intestines, and possibly the kidneys as well.

Regarding access to the lungs, it is important to note that the ultrasonic waves do not propagate in air. In the event that a low frequency elastic wave is detected on the basis of an ultrasonic signal reflected by liver 16, this characteristic precludes the possibility that the low frequency elastic wave may have been generated in the lungs.

Regarding access to the intestines, it is known that the intestine wall is too thin to allow detection of a low frequency elastic wave.

Regarding access to the kidneys, it is probable that a low frequency elastic wave may propagate in the kidneys. On the other hand, since the propagation of the low frequency elastic wave is monitored to a depth from 25 to 65 mm, the possibility of detecting a low frequency elastic wave in the kidneys is precluded.

In summary, for a non-limiting application of the method according to the invention, positioning of vibration elastography probe 10 between two of the four ribs 14 and detection of the propagation of a low frequency elastic wave (parameter of the liver 16) in region of interest 17 formed at a depth between 25 and 65 mm makes it possible to ensure that vibration elastography probe 10 is positioned correctly for the purpose of determining at least one property of liver 16.

Moreover, as was shown in the foregoing, the parameter of the liver 16 may be constituted by a physiological parameter, such as detection of a flow of blood by means of a Doppler echography. In such an embodiment, if the blood flow matches a reference blood flow, then vibration elastography probe 10 is positioned correctly for the purpose determining a property of the liver 16.

In general, it is understood that any representative parameter of the biological tissue may be used to validate the positioning of ultrasonic transducer 12. Equally, a plurality of parameters may be used to validate the positioning of ultrasonic transducer 12.

Moreover, several parameters may be combined to validate the presence of a target tissue opposite ultrasonic transducer 12. Thus, according to such an embodiment, a result obtained by a combination of these parameters is compared with a reference parameter, a property is determined (fifth step 5) only if the result arising from the combination is effectively similar to the value of the reference parameter. The parameters may be combined accordance with various models, such as, for example, a logistic regression type model. Logistic regression enables a prediction model to be constructed that includes the values of determined parameters.

By way of example, the value obtained from the combination may be obtains by the application of a formula of this type:

Prediction value (result obtained from the combination)=$a+b$*Parameter_1 [. . . ]+$c$*Parameter_2 [. . . ] . . .

It should be noted that the symbol "[. . . ]" represents a vector values that form a determined parameter.

Terms a, b and c are constants.

According to a fifth step 5, a property of the biological tissue is determined on the basis of the result obtained during the fourth, comparison step 4.

For example, if the absolute value of the difference between a parameter determined during third step 3 and the value of the corresponding reference value is less than a given threshold value, then a property of the biological tissue is determined.

In addition, according to another embodiment the parameter may be formed by values associated with the propagation of a low frequency elastic wave. These values may for example correspond to amplitude levels or image quality criteria.

According to such an embodiment, the result obtained in the course of fourth step 4 is formed by "detection of a low frequency elastic wave". If this low frequency elastic wave is detected, then a property of the biological tissue is determined.

To do this, the property of the biological tissue must be determined by following a procedure.

The procedure may be, in non-limiting manner a vibration elastography procedure initiated by a vibration elastography probe 10 in accordance with that initiated in the course of second step 2 or a procedure requiring simple ultrasonic emissions and acquisitions by means of an ultrasonic transducer 12. This embodiment may be used for the purpose of determining an ultrasonic attenuation generated by the biological tissue.

The determination of a property may be initiated automatically by software means (not shown) if the absolute value of the difference between the value of the parameter determined during third step 3 and the value of the reference parameter is less than a given threshold value. In other words, no action, no initiation to determine a property is performed by the operator.

Otherwise, determination of a property may be initiated manually by the operator pressing an initiation button (not shown), which may be included in probe 10, after receiving an acoustic and/or visual message (by means of an indicator) informing him that probe 10 is positioned correctly.

Many algorithms for measuring ultrasonic attenuation are described in the pertinent literature. For example, in non-limiting manner one may cite the ultrasonic attenuation evaluation algorithm called "Frequency-shift method", or "Zero-crossing method". The principle of this algorithm is described in document number U.S. Pat. No. 4,441,368.

In general, the central frequency of an ultrasonic signal is reduced as it passes through biological tissues. Consequently, an evaluation of the shift in the central frequency of the ultrasonic signal enables the ultrasonic attenuation to be evaluated. The central frequency of the ultrasonic signal may be estimated in the temporal domain by counting the number of times it passes through the zero point in a given timeframe.

In non-limiting manner, an algorithm for calculating ultrasonic attenuation may comprise the following steps:
  selecting a region of interest 17 for each radio frequency ultrasonic signal (in the example of the liver 16, region of interest 17 may be located between 25 and 65 mm below the epidermis 13, for example);

creating a time window framework for each radio frequency ultrasonic signal from region of interest 17, the number of windows being variable from 1 to n for an identical time period T, each window being overlapped by the neighbouring window by a preset percentage;

for each window, evaluating the number of times the radio frequency ultrasonic signal passes through the zero point; (accordingly, the more attenuated the radio frequency ultrasonic signal is, the greater the reduction in the number times it will pass through the zero point during a window of temporal duration T);

determining an ultrasonic attenuation value by means of a mathematical formula.

It should be noted that the ultrasonic attenuation of the same biological tissue varies if the tissue has a low content of fatty tissue or a high proportion of fatty tissue, because the impedance offered by the fat differs from that of soft tissues. Besides being representative of a target biological tissue, ultrasonic attenuation may make it possible to carry out a quantitative and/or qualitative evaluation of the proportion of fat that makes up the biological tissue being measured, for example in the liver 16 of our example.

Otherwise, during fifth step 5, the property of the biological tissue may be determined on the basis of data extracted from the acquisition of the at least one ultrasonic signal reflected by the biological tissue, which acquisition takes place in second step 2. This option is particularly advantageous because it requires only one measurement in order to carry out third step 3 (determining a parameter of the biological tissue by acquisition of the at least one ultrasonic signal reflected by the biological tissue) and fifth step 5 (determining a property of the biological tissue on the basis of the result of the comparison) at the same time. Consequently, the position of probe 10 has not been changed and the operator is able to affirm with certainty that the property obtained by implementing the method according to the invention corresponds to a property of the biological tissue he wishes to measure. In the example of the liver 16 that has served throughout this description, detection of the propagation of a low frequency elastic wave in the biological tissue of region of interest 17 may be used as a viscoelastic parameter that serves to verify that the measured tissue does match the target tissue, and once this assumption has been confirmed, the determination of the propagation speed of the low frequency elastic wave enables a property of the biological tissue measured to be estimated, that is to say its elasticity. Accordingly, only one measurement is necessary.

With the aid of the invention, measurement of at least one parameter of the biological tissue enable the elasticity of the biological tissue and/or the ultrasonic attenuation of a biological tissue to be determined quantitatively and/or qualitatively.

In general, when a determined viscoelastic and/or ultrasonic and/or physiological parameter of a biological tissue differs from the reference and/or ultrasonic and/or physiological parameter of the corresponding target tissue, a property cannot be determined. Thus, the characteristic value of the property obtained is representative of the biological tissue the operator wishes to measure. No specific knowledge is required in order to position the probe opposite the biological tissue. Moreover, the operator may perhaps be alerted as to the positioning of the probe and thus of the ultrasonic transducer opposite the target biological tissue by means of a device such as an indicator.

In other words, the method for measuring at least one property of a biological tissue in accordance with the invention makes it possible for an operator who does not possess specific knowledge in the human or animal realm to take measurements of the properties of a target biological tissue in order to determine, for example, the elasticity of the target biological tissue and/or the ultrasonic attenuation of the target biological tissue.

In addition, the invention has been described more particularly with reference to its application with an organ, the liver 16. However, it may also be desirable to apply the same method in the case of any type of human or animal organ, such as a breast, a fatty mass, a gland, a ganglion, either in-vivo or in-vitro, or even to carry out quality control in industrial applications, particularly agrifood applications.

The preceding description of the invention is intended for purely exemplary purposes, it is understood that one skilled in the art will be entirely capable of creating a number of different variations on the method for measuring at least one property of a biological tissue, particularly with respect to the parameters without thereby exceeding the limits of the patent.

The invention claimed is:

1. A method for measuring at least one property of a biological tissue, comprising:
    positioning an ultrasonic transducer opposite said biological tissue to be measured;
    using the ultrasonic transducer, generating at least one ultrasonic signal inside said biological tissue;
    using the ultrasonic transducer, acquiring at least one ultrasonic signal reflected by said biological tissue;
    determining at least one parameter of said biological tissue by acquiring said at least one ultrasonic signal reflected by said biological tissue, said at least one parameter being representative of said biological tissue, said at least one parameter being a viscoelastic parameter of said biological tissue;
    comparing said at least one parameter of said biological tissue with at least one reference parameter of a target biological tissue, said reference parameter being characteristic of the target biological tissue and sufficient to identify the target biological tissue, so as to confirm a hypothesis of the presence of said target biological tissue opposite said ultrasonic transducer, said comparing including comparing a value of the at least one determined parameter with a value of the at least one reference parameter; and
    determining at least one property of said biological tissue on the basis of a result of said comparing, the determining of the at least one property only being carried out if an absolute value of the difference between said value of the at least one determined parameter and said value of the at least one reference parameter is less than a given threshold value, said at least one property of said biological tissue being an ultrasound attenuation;
    wherein the steps of generating at least an ultrasonic signal, acquiring at least an ultrasonic signal, determining at least one parameter of said biological tissue and comparing said at least one parameter and said at least one reference parameter are repeated, after moving the ultrasonic transducer to a different position opposite said biological tissue, until the absolute value of the difference between said value of at least one determined parameter and said value of the at least one reference parameter is less than the given threshold value, the ultrasonic transducer being then confirmed to be opposite the target biological tissue.

2. The method as recited in claim 1, wherein a plurality of parameters are combined together, the comparing including comparing a result obtained from said combination of parameters with the at least one reference parameter.

3. The method as recited in claim 1, further comprising generating a low frequency elastic wave in said biological tissue.

4. The method as recited in any claim 3, wherein said low frequency elastic wave is generated by vibration of a low frequency elastic wave generator.

5. The method as recited in any claim 3, wherein said low frequency elastic wave is generated by radiation pressure.

6. The method as recited in claim 1, wherein an indicator informs an operator of the result of the comparing.

7. The method as recited in claim 1, wherein said at least one parameter and said at least one property of said biological tissue are determined on the basis of data extracted from said acquiring of the at least one ultrasonic signal reflected by the biological tissue.

8. The method as recited in claim 1, wherein said viscoelastic parameter is the elasticity of said biological tissue.

9. The method as recited in claim 8, wherein said elasticity is obtained by an elastography method.

10. A method for measuring at least one property of a biological tissue, comprising:
    positioning an ultrasonic transducer opposite said biological tissue to be measured;
    using the ultrasonic transducer, generating at least one ultrasonic signal inside said biological tissue;
    using the ultrasonic transducer, acquiring at least one ultrasonic signal reflected by said biological tissue;
    determining at least one parameter of said biological tissue by acquiring said at least one ultrasonic signal reflected by said biological tissue, said at least one parameter being representative of said biological tissue, said at least one parameter being a viscoelastic parameter of said biological tissue;
    comparing said at least one parameter of said biological tissue with at least one reference parameter of a target biological tissue, said reference parameter being characteristic of the target biological tissue and sufficient to identify the target biological tissue, so as to confirm a hypothesis of the presence of said target biological tissue opposite said ultrasonic transducer, said comparing including comparing a value of the at least one determined parameter with a value of the at least one reference parameter; and
    determining at least one property of said biological tissue on the basis of a result of said comparing, said at least one property of said biological tissue being determined on the basis of same data extracted from said acquisition of the at least one ultrasonic signal reflected by the biological tissue, the determining of the at least one property only being carried out if an absolute value of the difference between said value of the at least one determined parameter and said value of the at least one reference parameter is less than a given threshold value, said at least one property of said biological tissue being an ultrasound attenuation;
    wherein the steps of generating at least an ultrasonic signal, acquiring at least an ultrasonic signal, determining at least one parameter of said biological tissue and comparing said at least one parameter and said at least one reference parameter are repeated after moving the ultrasonic transducer to a different position opposite said biological tissue, until an absolute value of the difference between said value of at least one determined parameter and said value of the at least one reference parameter is less than a given threshold value, the ultrasonic transducer being then confirmed to be opposite the target biological tissue.

11. The method as recited in claim 10, wherein said at least one parameter corresponds to a measurable value of an intrinsic characteristic of said biological tissue.

12. A method for measuring at least one property of a biological tissue, comprising:
    positioning an ultrasonic transducer opposite said biological tissue to be measured;
    using the ultrasonic transducer, generating at least one ultrasonic signal inside said biological tissue;
    using the ultrasonic transducer, acquiring at least one ultrasonic signal reflected by said biological tissue;
    determining at least one parameter of said biological tissue by acquiring said at least one ultrasonic signal reflected by said biological tissue, said at least one parameter corresponding to a measurable value of an intrinsic characteristic of said biological tissue; said at least one parameter being a viscoelastic parameter of said biological tissue;
    comparing said at least one parameter of said biological tissue with at least one reference intrinsic parameter of a target biological tissue, said reference intrinsic parameter being characteristic of the target biological tissue and sufficient to identify the target biological tissue, so as to confirm a hypothesis of the presence of said target biological tissue opposite said ultrasonic transducer, said comparing including comparing a value of the at least one determined parameter with a value of the at least one reference parameter; and
    determining at least one property of said biological tissue on the basis of a result of said comparing, the determining of the at least one property only being carried out if an absolute value of the difference between said value of the at least one determined parameter and said value of the at least one reference parameter is less than a given threshold value, said at least one property of said biological tissue being an ultrasound attenuation;
    wherein the steps of positioning of the ultrasonic transducer opposite the biological tissue, generating at least an ultrasonic signal, acquiring at least an ultrasonic signal, determining at least one parameter of said biological tissue and comparing said at least one parameter and said at least one reference intrinsic parameter are repeated after moving the ultrasonic transducer to a different position opposite said biological tissue, until an absolute value of the difference between said value of at least one determined parameter and said value of the at least one reference intrinsic parameter is less than a given threshold value, the ultrasonic transducer being then confirmed to be opposite the target biological tissue.

13. The method as recited in claim 12, wherein said at least one parameter and said at least one property of said biological tissue are determined on the basis of same data extracted from said acquiring of the at least one ultrasonic signal reflected by the biological tissue.

* * * * *